(12) United States Patent
Varhaniovszki

(10) Patent No.: US 8,210,059 B2
(45) Date of Patent: Jul. 3, 2012

(54) METHOD OF INSPECTING BEVERAGE BOTTLES FOR CONTAMINATION IN A BEVERAGE BOTTLE FILLING PLANT, A METHOD OF INSPECTING CONTAINERS FOR CONTAMINATION IN A CONTAINER FILLING PLANT, AND AN ARRANGEMENT THEREFOR

(75) Inventor: Gyula Varhaniovszki, Waltrop (DE)

(73) Assignee: KHS AG, Dortmund (DE)

( * ) Notice: Subject to any disclaimer, the term of this patent is extended or adjusted under 35 U.S.C. 154(b) by 318 days.

(21) Appl. No.: 12/465,387

(22) Filed: May 13, 2009

(65) Prior Publication Data

US 2010/0116026 A1    May 13, 2010

Related U.S. Application Data

(63) Continuation-in-part of application No. PCT/EP2007/009634, filed on Nov. 7, 2007.

(30) Foreign Application Priority Data

Nov. 13, 2006  (DE) .......................... 10 2006 053 673

(51) Int. Cl.
*G01N 21/90* (2006.01)
(52) U.S. Cl. ....................................... 73/865.8
(58) Field of Classification Search ............ 73/1.02, 73/865.8, 865.9, 866
See application file for complete search history.

(56) References Cited

U.S. PATENT DOCUMENTS

| | | | | |
|---|---|---|---|---|
| 5,376,550 A | * | 12/1994 | Fine et al. ........................ | 436/47 |
| 5,397,540 A | * | 3/1995 | Rounbehler et al. ........ | 422/82.08 |
| 5,435,198 A | | 7/1995 | Rounbehler et al. | |
| 5,520,060 A | * | 5/1996 | Gysi et al. ..................... | 73/865.8 |
| 5,571,978 A | | 11/1996 | Gysi et al. | |
| 6,013,228 A | * | 1/2000 | Achter et al. .................... | 422/66 |
| 2010/0116295 A1 | * | 5/2010 | Molitor et al. .................. | 134/23 |

FOREIGN PATENT DOCUMENTS

| | | |
|---|---|---|
| CN | 1102882 A | 5/1995 |
| DE | 92 10 531 | 7/1993 |
| DE | 203 01 224 | 3/2004 |
| DE | 10 2004 034 852 | 2/2006 |
| DE | 10 2004 048146 | 4/2006 |
| EP | 0 759 330 | 2/1997 |
| EP | 1 619 493 | 1/2006 |

OTHER PUBLICATIONS

International Search Report PCT/EP2007/009634 and English translation thereof.
International Preliminary Report on Patentability PCT/EP2007/009634 and English translation thereof.
English translation of Chinese Office Action 200780030398.1.

* cited by examiner

*Primary Examiner* — Eric S McCall
(74) *Attorney, Agent, or Firm* — Nils H. Ljungman & Associates

(57) ABSTRACT

Method and apparatus for determining presence or absence of contamination in bottles or similar containers, in which a first fluid medium is introduced into a container, and then a second, different, fluid medium is introduced into the container to thus form a third fluid medium in the container. A portion of the third fluid medium is then removed from within the container by suction. Finally, the portion of the third fluid medium is sensed in a sensor apparatus to determine presence or absence of contamination in the portion of the third fluid medium.

19 Claims, 8 Drawing Sheets ated in the inspection liquid and/or the control liquid. Occurring subsequently is the withdrawal of a respective sample and the following analysis of a test sample that was taken from the respective container; and such a sample may comprise, in part, the inspection liquid available in the container, the control liquid available in the container, and/or, also part of a gas housed in the container.

METHOD OF INSPECTING BEVERAGE BOTTLES FOR CONTAMINATION IN A BEVERAGE BOTTLE FILLING PLANT, A METHOD OF INSPECTING CONTAINERS FOR CONTAMINATION IN A CONTAINER FILLING PLANT, AND AN ARRANGEMENT THEREFOR

CONTINUING APPLICATION DATA

This application is a Continuation-In-Part application of International Patent Application No. PCT/EP2007/009634, filed on Nov. 7, 2007, which claims priority from Federal Republic of Germany Patent Application No. 10 2006 053 673.8, filed on Nov. 13, 2006. International Patent Application No. PCT/EP2007/009634 was pending as of the filing date of this application. The United States was an elected state in International Patent Application No. PCT/EP2007/009634.

BACKGROUND

1. Technical Field

The present application relates to a method of inspecting beverage bottles for contamination in a beverage bottle filling plant, a method of inspecting containers for contamination in a container filling plant, and an arrangement therefor.

2. Background Information

Background information is for informational purposes only and does not necessarily admit that subsequently mentioned information and publications are prior art.

The present application relates to a procedure for the inspection of bottles, or such like containers, as well as a measuring station for an inspection distance, or control distance for bottles, or such like containers.

The present application relates to a procedure, or method, for the inspection by bottles, or such like containers, in which there is introduced, into each container, an inspection liquid and/or control liquid. At least a test sample of this inspection liquid and/or control liquid or a test sample of gases in the container is taken from every container in a measuring phase and is inspected for the presence or absence of a possible contamination or is analyzed. Also, the present application relates to a measuring station of an inspection distance, control distance, or section for the inspection of bottles or such like containers. The measuring station comprises means for taking at least one test sample of a previously introduced inspection liquid, control liquid, and/or gaseous reaction products from the containers, as well as means for examining and analyzing the respective test sample.

Inspection distances or control distances, i.e. portions of a pertaining conveyer system of the production line, hereinafter also referred to as measuring sections, of predetermined lengths of a transport means or a conveyor for bottles or such like containers are used for example in production lines for bottling, that is for filling liquid goods into containers; in addition, the containers are to be checked prior to filling for possible contamination, so that contaminated containers can be removed from the production line even prior to filling, or in one possible embodiment, prior to the cleaning step that may be done prior to filling. For this investigation of any contamination, it is also possible to introduce into the container a measured volume or quantity of an inspection liquid and/or control liquid that is configured to dissolve any contaminants, i.e., with a defined, or fixed, given volume, in each case, so that any contaminations present in the containers (e.g., dirt, or other foreign matters, germs, etc.) are substantially dissolved in the inspection liquid and/or the control liquid. Occurring subsequently is the withdrawal of a respective sample and the following analysis of a test sample that was taken from the respective container; and such a sample may comprise, in part, the inspection liquid available in the container, the control liquid available in the container, and/or, also part of a gas housed in the container.

In at least one possible embodiment, the inspection of the containers occurs between the cleaning of the containers and the filling of the containers. In such an embodiment, if a container is not cleaned sufficiently by the cleaning machine, the container may be inspected and then re-sent through the cleaning machine for further cleaning. Once the container is sufficiently clean, the container may then move on to the filling machine to be filled.

In at least one possible embodiment of the present application, the inspection of the bottles or containers may occur before the cleaning of the containers in the cleaning or rinsing machine. In such an embodiment, the inspection machine may check for contaminants which may not be able to be cleaned by the cleaning or rinsing machine. Any containers found to be contaminated may then deemed unuseable and may be taken out of the production line. Containers that are not contaminated may continue to the cleaning machine and subsequently to the filling machine.

It is not only a condition for a proper inspection of the containers that the inspection liquid and/or control liquid is introduced in exactly or generally measured amounts into a respective container, i.e., the amount of the inspection liquid and/or control liquid is substantially constant for all or substantially all or most containers, within narrow limits, but also that the withdrawal of the test samples occurs in reproducible manner or is steady, i.e. for example in the way that the portion or the amount of the inspection liquid, the control liquid, and/or the respective gas in the respective test will be substantially within narrow limits for all or substantially all or most containers.

OBJECT OR OBJECTS

An object of the present application is to provide or indicate a procedure or method for the inspection of bottles, or such like containers, which delivers exact or substantially exact or general measuring results and results of analyses also in the case of a high production rate of the production line (high number of processed containers per time unit).

SUMMARY

For the solution of this task or object, a procedure is taught that is in accordance with a procedure for the inspection by bottles or such like containers in which there is introduced, into the container, an inspection liquid and/or control liquid, and at least a test sample of this inspection liquid and/or control liquid or a test sample of gases from the container is taken from every container in a measuring phase. The test sample is inspected for the presence or absence of a possible contamination or is analyzed. The withdrawal of the at least one test sample is taken during the measuring phase, by effectuating of at least one measuring gas impulse into the respective container, as well as by removing, by suction, from the respective container of a gas comprising the inspection liquid and/or control liquid, which gas is to be analyzed. A measuring station with an inspection distance, measuring distance, or production line section that is configured for the inspection, testing, or examination of bottles or such like containers to establish the presence of a possible contamination, is an object of a measuring station of an inspection distance, control distance, or section for the inspection of bottles or such like containers, with means for taking, in each case, at least one test sample of a previously introduced inspection liquid, control liquid, and/or gaseous reaction products from the containers, as well as for examining and analyzing the respective test sample. The means for taking of the at least one test sample from the respective container comprise dock-able measuring heads with at least one first measuring-head opening for the introduction, by way of an impulse, of a measuring gas under pressure, into the respective container. The means also comprise at least one second measuring-head opening configured to supply the at least one test sample of analysis gas comprising the inspection liquid and/or control liquid, for instance in mist form, from the respective container to an analysis unit.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

Further details of the present application are described according to the present application. The present application is explained in greater detail in the following with reference to the drawing figures showing the arrangement of several embodiments of the present application. There is shown in.

DESCRIPTION OF EMBODIMENT OR EMBODIMENTS

Figure 1:
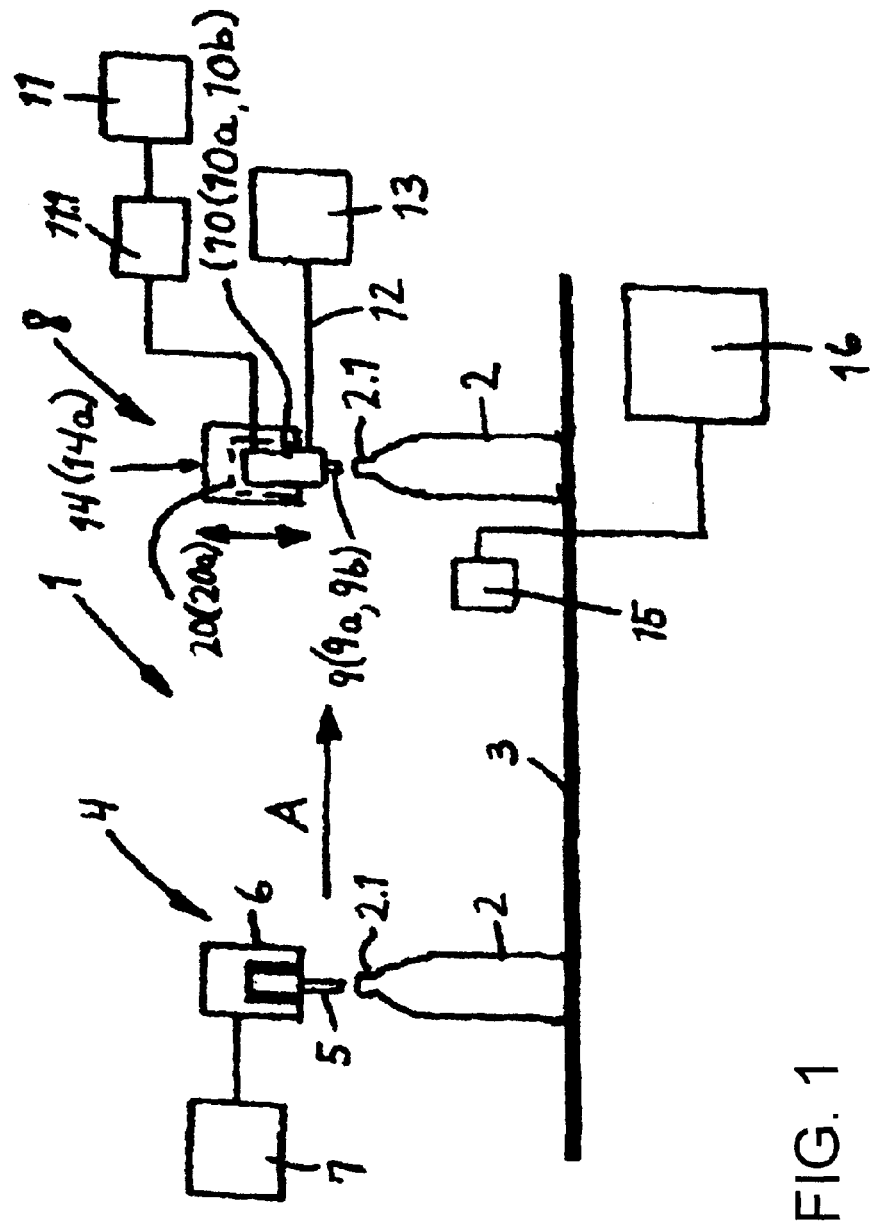
FIG. 1 in schematic representation, an inspection section, inspection distance, or control distance for bottles with an analysis station, or measuring station according to the present application.

In the figures, in general, reference numeral 1 designates a measuring distance of a conveyer system 3 on which the bottles 2 are moved while in the upright standing attitude, i.e. with the respective bottle axis being disposed in the vertical direction, as a single-track bottle stream, moving in the direction of transport or travel as is indicated by arrow A; namely, with the shown embodiment form, such that the bottles 2 are disposed in close proximity with respect to one another in this bottle stream, i.e. these bottles are supplied to the measuring section by being respectively pushed.

A station 4 is provided for the measured introduction of a control liquid and/or inspection liquid into the bottles 2; the station 4 being provided at the conveying region of the conveyer system 3. This control liquid or inspection liquid is, for instance, sterile water or another liquid which liquid is substantially compatible, acceptable, or neutral with respect to the product that is later to be bottled into the bottles 2 or, however, the liquid may comprise the product that is later to be bottled.

Likewise, an inspection liquid can be also used which substantially reacts chemically in the usual manner of reaction, and by such reaction forms, in one possible embodiment, easily provable, liquid or gaseous reaction products; and which liquid is removed again after the completed control, inspection, or testing from the bottles 2.

The station 4 comprises a nozzle tube 5, by means of which the control liquid and/or inspection liquid is introduced, in a precisely or generally predetermined given or measured amount into every bottle 2, and this occurs due to a drive arrangement 6 which is configured to impart an impulse, pulse, or pulsating movement, upon the inspection liquid, in one possible embodiment. Then when a bottle 2 has reached the station 4, by the nozzle tube 5 being lowered, through the bottle mouth 2.1, into the relevant bottle; and then the nozzle tube 5 is passed together with the bottle 2 along the production path, and subsequently, the nozzle tube 5 is removed from the pertaining bottle 2. The drive arrangement 6 that is configured to provide a driving movement is additionally configured in such a way that, on this occasion, i.e. when the nozzle tube 5 is removed from the pertaining bottle, the nozzle tube 5 carries out a lifting movement comprising a substantially vertical movement-component, and/or substantially horizontal movement-component. The inspection liquid and/or control liquid is provided by a stock, supply, or source generally identified by reference numeral 7.

Next to the station 4, when viewed in the transport direction as is indicated by arrow A; either directly or indirectly, there is disposed a measuring station 8 in which at least one test sample is taken from each bottle 2. When speaking of these test samples, these may comprise, depending on the method that is utilized, a portion of the inspection liquid and/or control liquid that was introduced into the bottles 2, and this liquid or fluid comprises, as one possibility, contaminations accepted by the fluid as solids or contaminants that are readily dissolved in the fluid (for example, foreign matters, germs, etc.) or, however, also reaction products of every bottle 2. Likewise, the test samples taken from bottles 2 can comprise gaseous test samples, which gaseous test samples, for instance, comprise gaseous reaction products of possible contaminations obtained by the reaction of contaminants with the inspection fluid.

In any case, the taken test sample is subsequently analyzed for contamination.

So as to essentially assure or promote a very high concentration of contaminants in the inspection liquid, and/or control liquid, or, however, also to essentially ensure or promote that a sufficient amount of reaction products is obtained, the measuring station 8 is positioned, when viewed in the transport direction A, away from the station 4 at such a distance that even in the event of a peak production rate of the measuring distance, and/or inspection distance 1, or section a sufficient reaction time or duration of reaction is attained for the inspection liquid, and/or the control liquid.

For the withdrawal of the test samples then when a bottle 2 has reached the measuring station 8, there is introduced, in its commencement attitude, from a position or level that is above the path of movement A of the bottle mouths 2.1, a measuring probe 9 of a measuring head 10 of the measuring station 8 into the bottle mouth 2.1 of the relevant bottle; and the bottle mouth 2.1 is then closed by the measuring head 10. Subsequently, the measuring probe 9, which is extending with its free end substantially below the bottle mouth 2.1 into the relevant bottle 2, introduces a precisely or substantially precisely or generally defined volume of a measuring gas, which is brought under pressure into the bottle interior; the pressure being in one possible embodiment configured such that it comprises a pressure impulse, namely, as is controlled by way of a control valve equipment 11.1 which is fed from a source of this measuring gas, for instance, the measuring gas being in the form of sterile air that is provided from a source 11 thereof.

At the same moment, or, however, in a condition of time-shift or time-offset condition a gas to be analyzed or an air and gas mixture, which is hereinafter also referred to as analysis gas, and which comprises, at least, a part of the inspection liquid and/or control liquid, in finely divided form, as was attained by the pressure impulse, this finely divided form including a pertaining mist or fog or, however, also a portion of the gaseous reaction products is evacuated by suction from the bottle 2, by the measuring head 10, and is supplied by way of the conduit arrangement 12 to an analysis unit 13.

At least one analysis occurs in the analysis unit 13, in one possible embodiment, however, repeated analyses, for instance, double or triple analyses are performed upon each test sample of the analysis gas taken by suction by way of the conduit arrangement 12. For the introduction of the measuring gas impulse, for the nebulization, or for creation of a mist, as well as for the removal of the analysis gas by suction, the measuring probe 9 and/or the measuring head 10, not only are configured such that they form separate canals or channels for the introduction of the measuring gas and for the removal of the analysis gas by suction, but they are in one possible embodiment configured so that an opening, serving for the introduction of the measuring gas impulse, of the measuring probe 9 is surrounded or concentrically disposed with respect to at least one opening of the measuring head 10 which is configured to remove the analysis gas by suction; thus, the analysis sample removal opening of the measuring head 10 may comprise an opening arrangement, i.e. e.g. may be in the form of a ring-shaped opening, or several individual openings.

In at least one possible embodiment of the present application, sodium carbonate may be introduced into the container or bottle 2, and may mix with any substances or contaminants in the bottle 2. The measuring head 10 permits the flow of the sodium carbonate and any additional substances or contaminants in the bottle 2 into the conduit 19.1 and connecting pipe or conduit 12 to the analysis unit 13, in which this mixture is heated to convert ammonia and amines to nitric oxide, mixing the products of heating with ozone to generate a chemical reaction which causes chemiluminescence and optically analyzing the resulting radiation to determine the presence or absence of ammonium salts or amine salts in the container. The inspection apparatus of the present application may include an ammonium sensor and/or an amine sensor for the detection of ammonium salts and/or amine salts. However, the present application may also comprise additional sensors for the detection of other contaminants in the containers 2.

In other words and in accordance with at least one possible embodiment of the present application, the inspection arrangement or apparatus may comprise a sensor which detects the presence of at least one contaminant present in a container or bottle 2. The apparatus may also comprise a sensor which determines the level of at least one contaminant present in the container 2 or measures the amount of at least one contaminant present in the container 2. Depending on the liquid material to be bottled in the containers 2, different levels of contaminants may be considered allowable in the containers 2. For example, alcoholic beverages may tolerate a higher level of contaminants present in the container 2 to be filled than fruit juices. A control device is provided, which stores the acceptable level. When the sensor determines the level of at least one contaminant present in the container 2 to be filled, the sensor may send a signal to the control device. The control device may then compare the determined level in the container 2 with the stored level in the control device. If the level of contamination in the container 2 is over the stored level in the control device, the container 2 may then be removed from the conveyor 3. If the level of contamination in the container 2 is below the stored level in the control device, the container 2 may then continue on the conveyor 3 to the next station in the production line. The level stored on the control device may be changed, depending on the liquid to be filled in the containers 2.

Because the bottles 2 are also moved by the conveyer system 3 during the introduction of the measuring gas impulse, as well as during the removal by suction of the analysis gas, movement being in the transport direction indicated by the arrow A, a drive arrangement 14 is provided for the measuring head 10, which drive arrangement 14 effectuates a lifting movement for the measuring head 10, which movement comprises a vertical component, namely, for the lowering of the measuring head 10, for the purpose of positioning of the measuring head 10 onto a bottle 2, or for the raising of the measuring head 10 from the respective bottle 2, as well as a horizontal movement-component, namely, for the carrying of the measuring head 10 along with the respective bottle 2, during the measuring phase, and for the return of the measuring head 10 into its commencement position upon completion of the respective measuring phase. By way of a control equipment 15, the drive arrangement 14, and, with it, the movement of the measuring head 10, are controlled in terms of movement; and, in one possible embodiment, the movement being subject to the operation of at least one sensor 16 that is configured to sense or grasp the position of the bottles 2; in one possible embodiment, also as a function of the present rate of the bottling equipment, and, therefore, also as a function of the transport speed of the conveyer system 3, namely, so that in order to achieve a very long or sufficiently long contact time or intervention time between the measuring head 10 and a bottle 2, during the measuring phase, the drive arrangement 14 is activated just shortly prior to a bottle 2 having actually reached the measuring station 8, namely, in such a way that delays, caused by the mass inertia, would not shorten the contact time, during which the measuring head 10 is contacting a bottle 2 and/or during which the measuring head 10 is docked to a bottle 2, and thus, the drive arrangement 14 is already actuated just prior to the actual arrival of a bottle 2 at the measuring station 8, but then when a bottle 2 is moved to the measuring station 8; and onto this bottle 2 or the relevant bottle mouth 2.1, the measuring head 10 is put on substantially without delay. For this to occur, it is necessary and/or desired to determine not only the optimum time for commencement of the movement of the measuring head 10, but also to determine by computer means, for this movement, as a function of the rate of production of the equipment, firstly, accelerations; secondly, delays; and, thirdly, the maximum speed, and subsequently to have the drive of the measuring head proceed with the respective course pertaining to these parameters. This approach or procedure is likewise a component of the present application.

The described measuring distance, inspection distance, and/or section 1 is suited, in one possible embodiment, for installations that are configured for cold-aseptic bottling of liquid filling goods, for instance, for cold-aseptic bottling of liquids intended to be drinks.

In the event that contamination of a bottle 2 is ascertained in the analysis, such bottle 2 is removed as being useless. In the case of very stringent requirements for the sterility of the containers 2, it can also be necessary and/or desired to preclude a group of bottles that comprises a contaminated bottle 2, from the further processing, or, respectively, remove such a group from the production line as being useless. The bottles 2 are, for instance, plastic bottles, e.g., PET reusable bottles.

Figure 2:
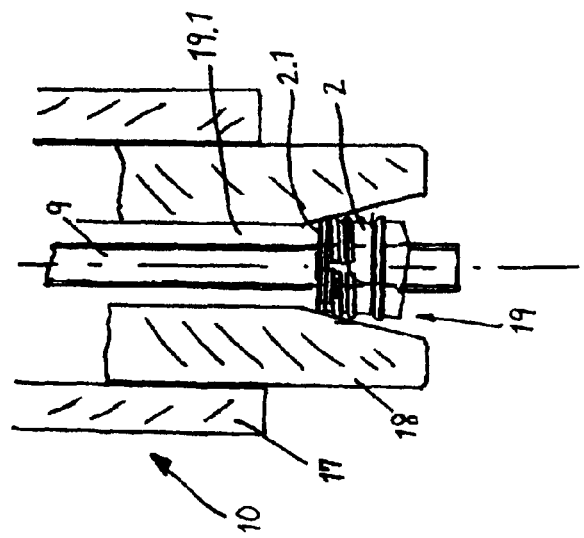
FIG. 2 in simplified representation, a cut or sectional view, at the measuring head of the measuring station in accordance with the embodiment in accordance with FIG. 1.

FIG. 2 shows the measuring head 10 in greater detail. This head has, among other things, a seal element arrangement 18 that is disposed in the measuring-head housing 17, which seal element arrangement or seal arrangement 18 is configured to serve, at the same time, as a centering cone for the bottles 2. During the introduction of the measuring gas and during the withdrawal of the test sample, or, respectively, during the withdrawal of the analysis gas, the seal element arrangement 18 lies in sealing manner against the bottle mouth 2.1, namely, in the area of a conical extension, or widening of a canal or channel 19 that is formed in the sealing element arrangement 18. The probe pipe 9, in the case of this embodiment of execution, merely serves for the introduction of the measuring gas or measuring gas impulse into the respective bottle, and during the measuring phase, the free end of probe pipe 9 reaches into the bottle 2, and is arranged with its end somewhat below the edge of the bottle mouth 2.1. The probe pipe 9 and the surrounding canal or channel 19 form a ring canal or channel 19.1 by means of which the analysis gas is removed by suction; by way of which removal the analysis gas is passed to the analysis unit 13. It will be appreciated that this ring canal or channel 19.1, while being closed to the outside, extends operatively into the conduit arrangement 12.

By way of the housing 17 the measuring head 10 is fastened, by way of one of the drive arrangements 14, to a measuring-head carrier 20 which measuring-head carrier 20 is moved as described herein above. In order so as to compensate tolerances at the height or level of the bottles 2, and so as to essentially ensure or promote a solid contact between the sealing element arrangement 18 at the respective bottle 2 during the introduction of the measuring gas impulse and during the withdrawal of the analysis gas, this sealing arrangement 18 is configured so as to be elastic, like rubber, for instance, and/or it is configured and disposed so as to be axially adjustable, and, further, is disposed in pre-stressed condition in the housing 17, by means that are configured to effectuate pre-stressing of the sealing element 18.

Figure 3:
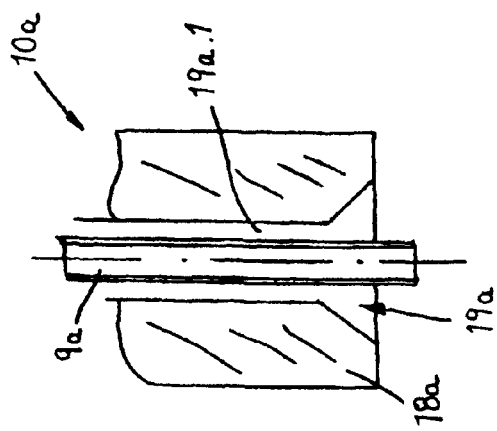
FIGS. 3 and 4 in representations similar to that of FIG. 2, further embodiments of the measuring head of the measuring station.

FIG. 3 shows in very simplified representation, as a further execution embodiment, a measuring head 10a which differs from the measuring head 10 merely by the fact that the angle of the cone of the recess 19a, which is enlarged at the underside of the sealing element arrangement, or centering element 18a is greater than the angle of the cone of the recess 19, so that already upon a very short vertical lifting stroke of the measuring head 10a occurring, the tight sealing arrangement between the bottle mouth 2.1 and the sealing element 18a is reached.

Figure 4:
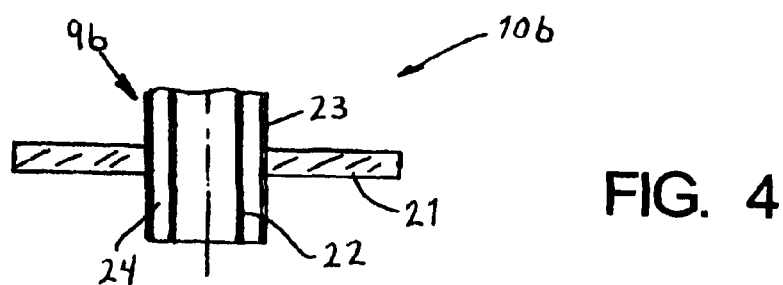

FIG. 4 shows in very simplified representation as a further execution embodiment a measuring head 10b which comprises basically a measuring pipe or probe pipe 9b, as well as of a planar element, for instance, a level disc that is configured as cover element or fastener element 21 which closes the bottle mouth 2.1 of the relevant bottle 2 during the respective measuring phase. The measuring pipe 9b projects with its free end below the underside of the fastener element 21 and, accordingly, during the measuring phase extends with this free end into the respective bottle 2.

In accordance with FIG. 5, the measuring pipe or probe pipe 9b comprises an inner pipe piece 22 and an external pipe piece 23, with the latter pipe piece 23 being concentrically disposed in reference to the inner pipe piece 22. Both pipe pieces 22 and 23 are open at the free end of the measuring pipe 9b. The pipe piece 22 forms the canal or channel for supplying of the measuring gas impulse. By way of the annular canal or channel 24 that is extending between the pipe pieces 22 and 23, the analysis gas is removed by suction. Optimum conditions are attained with this embodiment form by the arrangement of the ring canal or channel 24 around the pipe piece 22, or, respectively, around the canal or channel that is configured to introduce the measuring gas impulse with respect to rendering of the inspection liquid and/or control liquid as a mist, as well as with respect to the removal of the analysis gas by suction.

Because the cover element 21 is disposed during the measuring phase substantially level on the edge of the bottle mouth 2.1, this execution form also provides the possibility to use the smaller outer diameter of the measuring pipe 9b, this smaller outer diameter being smaller with respect to the diameter of the bottle mouth 2.1, for lengthening of the measuring time, i.e., for the lengthening of the time during which the measuring pipe 9b is introduced into the respective bottle 2. This is made clear by FIGS. 5A, 5B, and 5C, which together depict the positions of the pipe 9 in the bottle mouth 2.1.

Figure 5A:
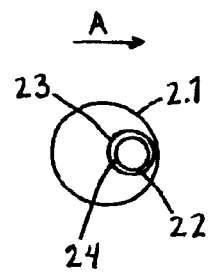
FIGS. 5A, 5B, and 5C in various positions in each case, sectional views through a measuring pipe or probe pipe of the measuring head in accordance with the embodiment of FIG. 4, together with a bottle mouth.
Figure 5B:
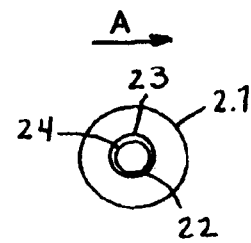
Figure 5C:
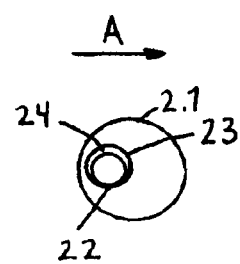

FIG. 5A shows the condition in which the measuring pipe 9b is introduced, at the beginning of the measuring process, into the bottle mouth 2.1. In this the axis of the measuring pipe 9b is disposed in offset manner with respect to the axis of the bottle mouth 2.1 when considered in the transport direction as is indicated by the arrow A. FIG. 5B shows the condition somewhat during the middle of the measuring phase, in which the measuring pipe 9b is disposed so as to be axis-aligned with the axis of the bottle mouth 2.1, i.e. the axes are disposed in coincidental manner with respect to one another. FIG. 5C shows the situation approximately at the completion of the measuring phase, in which the axis of the measuring pipe 9b is moved so as to be disposed in offset manner with respect to the axis of the bottle mouth 2.1 when considered with respect to the transport direction as is indicated by the arrow A; i.e. the axis of the measuring pipe 9b is disposed in offset manner in the direction that is opposite to the direction of travel as is indicated by arrow A.

Upon completion of every measuring phase, in one possible embodiment, a rinsing of the measuring heads 10, 10a, or, respectively 10b, and the connections between the measuring head and the analysis unit 13 occurs, for instance, by using the measuring gas (e.g., sterile air), so that the analysis of a measurement is not impacted or falsified by the remains from a preceding measurement in the measuring heads 10, 10a, 10b, and/or in the relevant connections or conduits.

Figure 6:
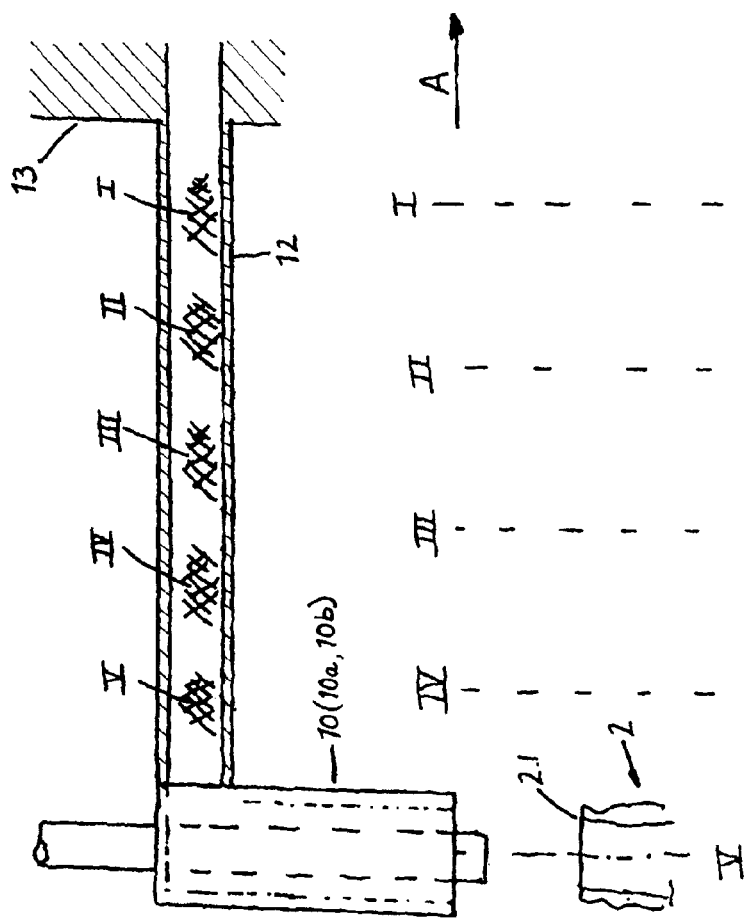
FIG. 6 in a simplified representation, the connection between the measuring head and the analysis unit.

Also other methods of measuring are possible, for instance, in the form as is illustrated by FIG. 6, wherein in the connection, respectively, in the conduit arrangement 12, between the measuring head 10, 10a, or 10b, and the analysis unit 13, at every point in time, in each case, several measurements of volumes of gas to be analyzed or test samples are taken, which volumes of gas or test samples originate from sequentially performed measuring, measurements, or measuring phases "I" to "V" which, accordingly, emanate from different containers; these gas volumes or test samples are brought sequentially to the analysis unit 13, or, respectively, are subjected to at least one analysis. This embodiment provides the advantage that dead-times are considerably reduced between the individual measuring phases and, therefore, a higher throughput rate, or processing speed, is possible for the measuring distance and/or inspection distance or section 1.

Figure 7:
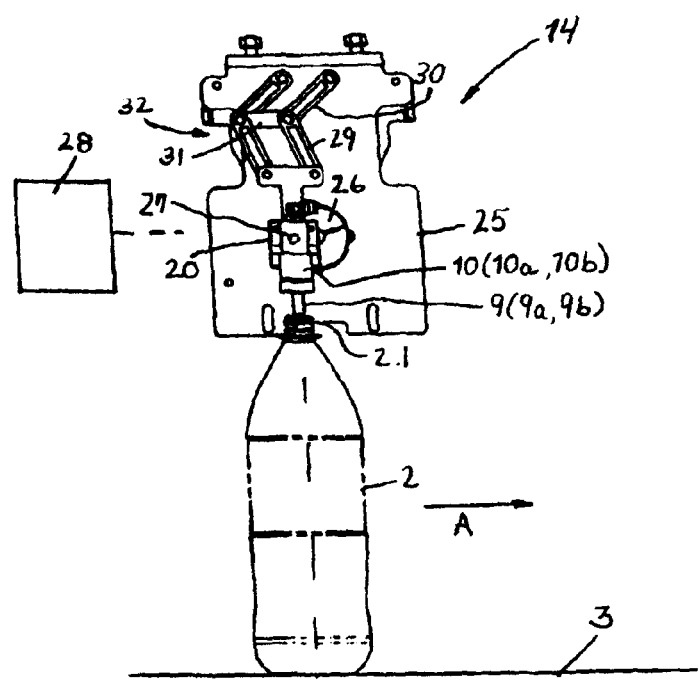
FIG. 7 in simplified representation, a measuring head of the measuring station, together with a conduit arrangement that is connected to an analysis unit.

FIG. 7 shows in greater detail an embodiment of the drive arrangement 14. This basically comprises a board or plate-like structure 25 which is fastened to a frame, not shown, of the measuring distance, inspection distance, and/or section 1; and in which a crank wheel 26 is provided that extends about a horizontal axis that is disposed vertically or substantially vertically with respect to the transport direction A, the crank wheel 26 being journaled so as to permit rotating movement. The measuring-head carrier 20, with the measuring heads 10, 10a, or 10b, is operatively connected to a crank pin 27 of the crank wheel 26 that can be operated by a drive arrangement 28. By way of a guide arrangement comprising a double-parallelogram guide arrangement 32 with parallelogram levers 29 and 30, as well as the coupling lever 31, the measuring-head carrier 20 is guided in such a way that it carries out the vertical movement and, at the same time, the horizontal lifting movement, while the crank wheel 26 is turning; and this is done, however, without a change of the orientation of the axis of the respective measuring head 10, 10a, or 10b.

Figure 8:
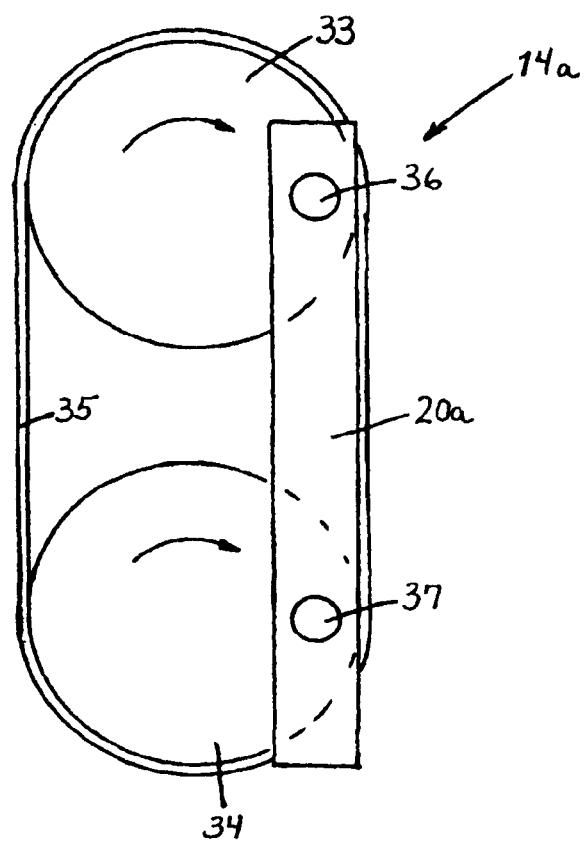
FIG. 8 in individual displays different drive, or impulse generators, or pulse generators of equipment that is configured to perform the lifting movement of the measuring head.

FIG. 8 shows a drive arrangement 14a which can be used instead of the drive arrangement 14 and shows, among other things, two gear wheels, or toothed wheels 33 and 34 configured to be engaged by a correspondingly configured belt with matching teeth. The two gear wheels 33 and 34 are oriented such that their axes are disposed parallel or virtually parallel with respect to each other in horizontal direction and again vertically to the transport direction A of the measuring distance, inspection distance, and/or section 1, that is the axis of the toothed wheel 33 is disposed in the vertical direction, atop the axis of the toothed wheel 34. Over the two toothed wheels 33 and 34, in which, for instance, the toothed wheel 33 is driven by the drive motor 28, there is passed a toothed belt 35 which is disposed so as to configure a closed loop. Each one of the toothed wheels 33 and 34 comprises a crank pin 36 or 37, respectively, which is journaled, respectively, in the measuring-head carrier 20a, namely, in such a way that the distance between the two crank pins 36 and 37 is equal to the distance between the axes of the toothed wheels 33 and 34, and the connecting line between the axes of the crank pins 36 and 37 extends parallel or virtually parallel to the connecting line of the axes of the toothed wheels 33 and 34. When activated or switched on, the drive motor 28, the measuring-head carrier 20a, and the relevant measuring head 10, 10a, or 10b affixed to the carrier 20a, are moved again with the necessary and/or desired lifting movement comprising the vertical and the horizontal components, namely, without change of the orientation of the axis of the respective measuring head.

Figure 9:
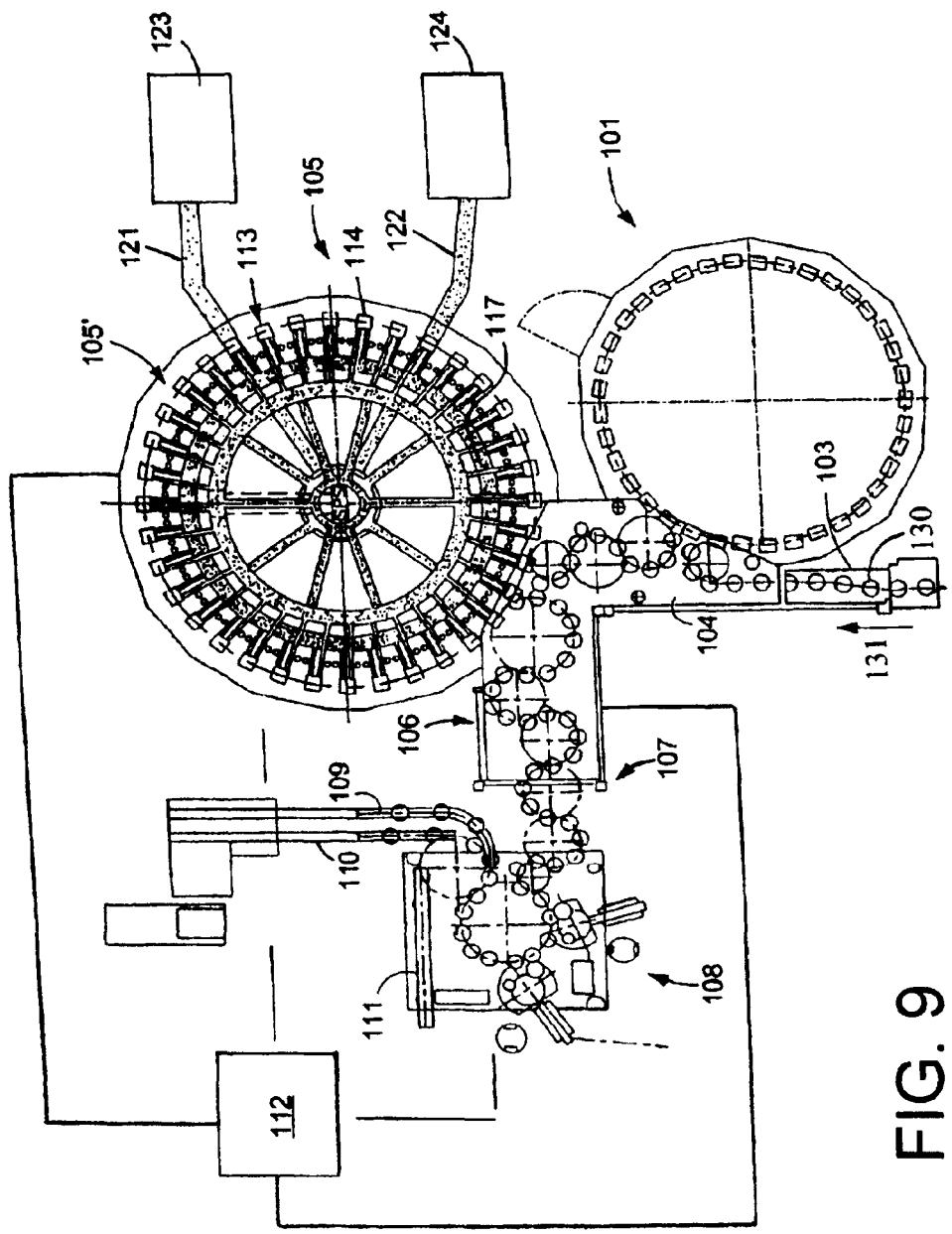
FIG. 9 shows schematically the main components of one possible embodiment example of a system for filling containers, for example a beverage bottling plant for filling bottles with at least one liquid beverage, in accordance with at least one possible embodiment, in which system or plant could possibly be utilized at least one aspect, or several aspects, of the embodiments disclosed herein.

FIG. 9 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 9 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 9, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

Figure 10:
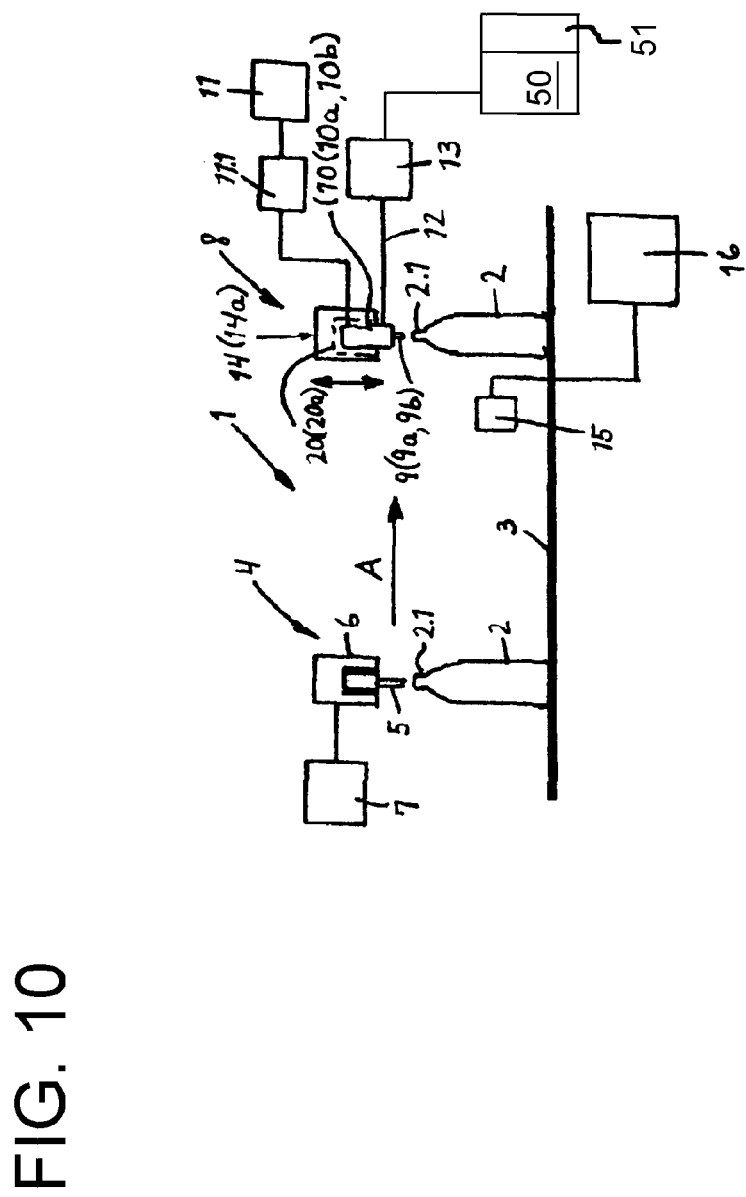
FIG. 10 shows an inspection section, inspection distance, or control distance for bottles with an analysis station, or measuring station according to the present application with a control device and a memory.

FIG. 10 shows an additional embodiment of the present application, in which the analysis unit 13 is operatively connected to a control device 50. The control device 50 comprises a memory 51. The memory 51 stores information relating to an acceptable level of contamination which may be present in the containers 2. The analysis unit 13 analyzes the test sample for the level of contamination, if any, in a container 2. This information is sent to the control device 50. The control device compares this determined level with the stored, acceptable level of contamination in the memory 51. If the control device 50 determines that the level of contamination in the container 2 is equal to and/or less than the predetermined, acceptable level, the container 2 may then continue on the conveyor 3 and then be moved to the next station in the production line. However, if the control device 50 determines that the level of contamination in the container 2 is greater than the predetermined, acceptable level, the container may then be taken out of or removed from the production line or stream of containers 2.

The present application was described herein with reference to several embodiments. It is understood that numerous changes as well as variations are possible, without thereby departing from the spirit and scope of the present application or the underlying thought or thoughts of the present application.

There is disclosed a procedure for the inspection of bottles, or such like containers, with which, into the respective container, a given amount of an inspection liquid, and/or control liquid is introduced and this liquid is analyzed for a possible contamination upon at least partial withdrawal thereof from the container.

One feature or aspect of an embodiment is believed at the time of the filing of this patent application to possibly reside broadly in the procedure for the inspection by bottles, or such like containers 2, in which method or procedure into the respective container 2 there is introduced an inspection liquid, and/or control liquid, and at least a test sample comprised of this inspection liquid, and/or control liquid, or a test sample of gases comprised in the container 2 is taken from every container 2 in a measuring phase and is inspected for the presence, or absence, of a possible contamination, or is analyzed, characterized thereby that the withdrawal of the at least one test sample is taken, during the measuring phase, by effectuating of at least one measuring gas impulse into the respective container 2, as well as by removing, by suction, from the respective container 2 of a gas comprising the inspection liquid, and/or control liquid, which gas is to be analyzed.

Another feature or aspect of an embodiment is believed at the time of the filing of this patent application to possibly reside broadly in the procedure, wherein the inspection liquid, and/or control liquid, is at least partially nebulized in the container 2 by at least one measuring-gas impulse.

Yet another feature or aspect of an embodiment is believed at the time of the filing of this patent application to possibly reside broadly in the procedure, wherein, in the container, the gaseous reaction products obtained by reaction of one of: [a.] the inspection liquid, and/or control liquid with [b.] any or all available contaminations in the container 2, are mixed, at least in part, by at least one measuring-gas impulse.

Still another feature or aspect of an embodiment is believed at the time of the filing of this patent application to possibly reside broadly in the procedure, wherein the respective container 2 is closed during the measuring phase.

A further feature or aspect of an embodiment is believed at the time of the filing of this patent application to possibly reside broadly in the procedure, wherein the introduction of the at least one measuring-gas impulse and the exhaust of the analysis gas occur at the same time, or substantially at the same time.

Another feature or aspect of an embodiment is believed at the time of the filing of this patent application to possibly reside broadly in the procedure, wherein the test gas, or the analysis gas, is removed, by suction using an under pressure, from the respective container.

Yet another feature or aspect of an embodiment is believed at the time of the filing of this patent application to possibly reside broadly in the procedure, wherein the measuring gas is introduced in a given volume into the respective container 2.

Still another feature or aspect of an embodiment is believed at the time of the filing of this patent application to possibly reside broadly in the procedure, wherein the measuring gas is introduced into the relevant container 2 using at least one measuring-gas impulse, of given impulse duration, with a given pressure, and/or with a predetermined temperature.

A further feature or aspect of an embodiment is believed at the time of the filing of this patent application to possibly reside broadly in the procedure, wherein the impulse duration of the at least one measuring-gas impulse is about thirty milliseconds in duration.

Another feature or aspect of an embodiment is believed at the time of the filing of this patent application to possibly reside broadly in the procedure, wherein the analysis of the analysis gas taken from the respective container 2 is carried out at least two times.

Yet another feature or aspect of an embodiment is believed at the time of the filing of this patent application to possibly reside broadly in the procedure, wherein in a storage 12 an intermediate storage is performed using several test samples of the analysis gas of in one possible embodiment different containers 2 and that the test samples are supplied from the storage 12 to analysis.

Still another feature or aspect of an embodiment is believed at the time of the filing of this patent application to possibly reside broadly in the procedure, wherein the storage 12 is configured by at least one conduit arrangement 12 between a measuring head 10, 10*a*, 10*b* and an analysis unit 13.

A further feature or aspect of an embodiment is believed at the time of the filing of this patent application to possibly reside broadly in the procedure, wherein the connecting canal or channel 12 is configured for the admission of a sequence of test samples of the analysis gas that is obtained from several containers 2.

Another feature or aspect of an embodiment is believed at the time of the filing of this patent application to possibly reside broadly in the procedure, wherein the measuring gas is introduced into a container 2 by way of at least one probe pipe, or measuring pipe 9, 9*a*, 9*b* that is configured to operatively extend into the respective container 2 by way of a container opening, or container mouth 2.1.

Yet another feature or aspect of an embodiment is believed at the time of the filing of this patent application to possibly reside broadly in the procedure, wherein the analysis gas is taken from the respective container by a canal or channel 19.1, 19*a*.1 that is disposed in sealing condition with respect to the container opening 2.1.

Still another feature or aspect of an embodiment is believed at the time of the filing of this patent application to possibly reside broadly in the procedure, wherein the analysis gas is taken from the respective container 2 by way of a measuring pipe, or probe pipe 9*b* configured to extend through the container opening 2.1 into the container 2.

A further feature or aspect of an embodiment is believed at the time of the filing of this patent application to possibly reside broadly in the procedure, wherein the measuring gas is sterile air.

Another feature or aspect of an embodiment is believed at the time of the filing of this patent application to possibly reside broadly in the procedure, wherein the containers 2 are moved during the measuring phase on a conveyer section 3, and that the measuring head 10, 10*a*, 10*b* that is configured for introduction of the measuring gas and for the withdrawal of the analysis gas, is further configured to be moved, at least during the measuring phase, together with the containers 2.

Yet another feature or aspect of an embodiment is believed at the time of the filing of this patent application to possibly reside broadly in the procedure, wherein the measuring head 10, 10*a*, 10*b* is moved for docking to the respective container 2 for the measuring phase, as well as for removing from this container 2 after the measuring phase, by a drive arrangement 14, 14*a*, so as to perform a lifting movement that comprises a vertical component, as well as a horizontal component.

Still another feature or aspect of an embodiment is believed at the time of the filing of this patent application to possibly reside broadly in the procedure, wherein the movement of the measuring head 10 away from a container 2 to the next following container 2 is determined computationally as a function of the position of the following container 2, and the present throughput, or production rate of the equipment with respect to accelerations, and/or delays, and/or maximum speed, and/or the respective course of these parameters, during the movement phase, at least at every change of the throughput, or production rate of the equipment.

One feature or aspect of an embodiment is believed at the time of the filing of this patent application to possibly reside broadly in a measuring station of an inspection distance, or control distance, or section 1 for the inspection of bottles, or such like containers 2, with means for taking, in each case, at least one test sample of a previously into the containers 2 introduced inspection liquid, and/or control liquid, or gaseous reaction products from the containers 2, as well as for examining and analyzing the respective test sample wherein the means for taking of the at least one test sample from the respective container 2 comprise dock-able measuring heads 10, 10*a*, 10*b* with at least one first measuring-head opening for the introduction, by way of an impulse, of a measuring gas under pressure, into the respective container 2, and with at least one second measuring-head opening 19.1, 19*a*.1, 24 configured to supply the at least one test sample of analysis gas comprising the inspection liquid, and/or control liquid, for instance, in mist form, from the respective container 2 to an analysis unit 13.

Another feature or aspect of an embodiment is believed at the time of the filing of this patent application to possibly reside broadly in the measuring station, comprising a controlled, the measuring gas under pressure providing source 11 which is controlled in such a way that the measuring gas is brought, in each case, in a given volume into the respective container 2.

Yet another feature or aspect of an embodiment is believed at the time of the filing of this patent application to possibly reside broadly in the measuring station, wherein the source 11, or a control valve arrangement 11.1 that is configured to control the amount of measuring gas that is introduced into the container 2, for the relevant control, are controlled in such a way that the measuring gas is brought into the respective container 2 with a pressure impulse of predetermined duration, with predetermined pressure, and/or with predetermined temperature.

Still another feature or aspect of an embodiment is believed at the time of the filing of this patent application to possibly reside broadly in the measuring station, wherein the source 11 providing the measuring gas, and/or the control valve arrangement 11.1 are controlled in such a way that the impulse duration of at least one measuring gas impulse amounts to thirty milliseconds.

A further feature or aspect of an embodiment is believed at the time of the filing of this patent application to possibly reside broadly in the measuring station, wherein the respective test sample is taken with an underpressure, or by suction from the respective container 2.

Another feature or aspect of an embodiment is believed at the time of the filing of this patent application to possibly reside broadly in the measuring station, comprising a storage 12 configured for storage, or intermediate storage, of several test samples of the analysis gas, in one possible embodiment taken from different containers, for a subsequent analysis.

Yet another feature or aspect of an embodiment is believed at the time of the filing of this patent application to possibly reside broadly in the measuring station, wherein the storage is configured by at least one connecting canal or channel 12 extending between the measuring head 10, 10*a*, 10*b* and the analysis unit 13.

Still another feature or aspect of an embodiment is believed at the time of the filing of this patent application to possibly reside broadly in the measuring station, wherein the at least one measuring-head opening for the introduction of the measuring gas into the respective container 2, is formed by an opening of a probe pipe, or measuring pipe 9, 9a, 9b disposed at the measuring head 10, 10a, 10b which probe can be introduced with its free end for the introduction of the measuring gas into the respective container 2 through a container opening 2.1.

A further feature or aspect of an embodiment is believed at the time of the filing of this patent application to possibly reside broadly in the measuring, wherein the measuring head 10, 10a, 10b is configured to assume a sealing position against the respective container, or its container opening 2.1.

Another feature or aspect of an embodiment is believed at the time of the filing of this patent application to possibly reside broadly in the measuring station, wherein the at least one second measuring-head opening is formed by an opening 19.1, 19a.1, 24 which surrounds, at least partially, at least one first measuring-head opening, or a measuring pipe, or probe pipe 9, 9a which forms this opening.

Yet another feature or aspect of an embodiment is believed at the time of the filing of this patent application to possibly reside broadly in the measuring station, wherein the measuring head 10, 10a, 10b is provided movably at the measuring station 8, namely, in such a way that this head 10, 10a, 10b is moved together, at least during the withdrawal of the respective test sample, with containers 2 that are moved on a transport section 3.

Still another feature or aspect of an embodiment is believed at the time of the filing of this patent application to possibly reside broadly in the measuring station, wherein the measuring head 10, 10a is disposed at the measuring station 8, so as to be movable in response to a drive arrangement 14, 14a that is configured for a lifting movement of the measuring head which lifting movement comprises a vertical movement-component, as well as also a horizontal movement-component.

A further feature or aspect of an embodiment is believed at the time of the filing of this patent application to possibly reside broadly in a method of inspecting beverage bottles for contamination in a beverage bottle filling plant, said method comprising the steps of: moving a first bottle into a first station with a conveyor system; introducing a liquid into said first bottle; moving said first bottle to a second station with said conveyor system; lowering a conduit arrangement into sealing engagement with said first bottle and lowering a pipe through the opening of said first bottle and into said first bottle; introducing a gas into said first bottle with said pipe of said conduit arrangement and forming a mist in said first bottle, which mist comprises said liquid and said gas; vacuuming a portion of said mist out of said first bottle with said conduit arrangement; flowing said portion of said mist from said conduit arrangement to an analysis unit; disengaging said conduit arrangement from said first bottle; analyzing said portion of said mist, with said analysis unit, for any contaminants and thereby inspecting said first bottle for the presence of contaminants; one of (A) and (B): (A) upon determining a presence of contaminants in said portion of said mist, removing said first bottle from said conveyor system; and (B) upon determining an absence of contaminants in said portion of said mist, moving said first bottle to a filling machine; and filling said first bottle with a beverage.

Another feature or aspect of an embodiment is believed at the time of the filing of this patent application to possibly reside broadly in a method of inspecting containers for contamination in a container filling plant, said method comprising the steps of: moving a first container into a first station; introducing a first fluid into said first container; moving said first container to a second station; introducing a second fluid into said first container and forming a mist in said first container; moving a portion of said mist out of said first container; flowing said portion of said mist to an analysis unit; analyzing said portion of said mist for any contaminants and thereby inspecting said first container for the presence of contaminants; one of (A) and (B): (A) upon determining a presence of contaminants in said portion of said mist, removing said first container from a stream of containers; and (B) upon determining an absence of contaminants in said portion of said mist, moving said first container to a filling machine; and filling said first container.

Yet another feature or aspect of an embodiment is believed at the time of the filing of this patent application to possibly reside broadly in a container inspecting arrangement for performing the method of inspecting containers for contamination in a container filling plant, said container inspecting arrangement comprising: a first moving arrangement being configured to move a first container into a first station; a first introducing arrangement being configured to introduce a first fluid into a first container; said first moving arrangement being further configured to move a first container to a second station; a second introducing arrangement being configured to introduce a second fluid into a first container and form a mist in the first container; a second moving arrangement being configured to move a portion of a mist out of a first container; a flowing arrangement being configured to flow a portion of a mist to an analysis unit; said analysis unit being configured to analyze a portion of a mist for any contaminants and thereby inspect a first container for the presence of contaminants; a removing arrangement being configured to, upon determining a presence of contaminants in a portion of a mist, remove a first container from a stream of containers; said first moving arrangement being further configured to, upon determining an absence of contaminants in a portion of a mist, move a first container to a filling machine; and said filling machine being configured to fill a first container.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report dated Mar. 27, 2008, and/or cited elsewhere are hereby incorporated by reference as if set forth in their entirety herein as follows: U.S. Pat. No. 5,435,198, having the title "SYSTEM FOR SAMPLING AND DETERMINING THE PRESENCE OF SALTS OF AMMONIA AND AMINES IN CONTAINERS," published on Jul. 25, 1995; DE 10 2004 048146, having the following English translation of the German title "TRAVELLING SAMPLING HEAD FOR MONITORING CONTAMINATION, IS SYNCHRONIZED TO ENGAGE, INJECT GAS, AND WITHDRAW SAMPLES OF FROM MOUTHS OF CONTAINERS MOVING ALONG A PRODUCTION LINE," published on Apr. 6, 2006; DE 92 10 531, having the German title "VORRICHTUNG ZUR INSPEKTION VON GEFÄSSEN," published Jul. 1, 1993; and DE 203 01 224, having the following English translation of the German title "FOREIGN GAS DETECTION APPARATUS, FOR CONTAINERS E.G. BOTTLES, HAS ADDITIONAL SAMPLING DEVICES," published on Mar. 11, 2004.

Some examples of inspection systems for inspecting containers for contaminants and methods for performing such inspections, which may possibly be utilized or adapted for use in at least one possible embodiment according to the present application may possibly be found in the following patents: U.S. Pat. No. 5,733,783, having the title "METHOD FOR SAMPLING AND DETERMINING THE PRESENCE OF CONTAMINANTS IN RECYCLABLE PLASTIC MATERIALS," published on Mar. 31, 1998; U.S. Pat. No. 5,688,693, having the title "METHOD AND SYSTEM FOR SAMPLING AND DETERMINING THE PRESENCE OF CONTAMINANTS IN RECYCLABLE PLASTIC MATERIALS," published on Nov. 18, 1997; and U.S. Pat. No. 5,569,606, having the title "METHOD AND SYSTEM FOR SAMPLING AND DETERMINING THE PRESENCE OF CONTAMINANTS IN RECYCLABLE PLASTIC MATERIALS," published on Oct. 29, 1996.

Some examples of ammonium sensors, which may possibly be utilized or adapted for use in at least one possible embodiment according to the present application may possibly be found in the following patents: U.S. Pat. No. 7,341,694, having the title "AMMONIA SENSOR," published on Mar. 11, 2008; U.S. Pat. No. 6,107,099, having the title "HYDROPHOBIC FLUORESCENT POLYMER MEMBRANE FOR THE DETECTION OF AMMONIA," published on Aug. 22, 2000; U.S. Pat. No. 4,961,834, having the title "ELECTROCHEMICAL MEASURING CELL FOR AMPEROMETRICALLY DETERMINING AMMONIA AND DERIVATIVES THEREOF," published on Oct. 9, 1990; U.S. Pat. No. 4,297,173, having the title "METHOD FOR DETERMINING AMMONIA AND SENSOR THEREFOR," published on Oct. 27, 1981; and U.S. Pat. No. 7,442,555, having the title "AMMONIA GAS SENSOR METHOD AND DEVICE," published on Oct. 28, 2008.

Some examples of amine sensors, which may possibly be utilized or adapted for use in at least one possible embodiment according to the present application may possibly be found in the following patents: U.S. Pat. No. 7,186,799, having the title "PEPTIDE AND AMINE EXAMINATION METHOD USING THE SAME," published on Mar. 6, 2007; U.S. Pat. No. 6,924,147, having the title "METHOD OF MAKING A POLYMERIC FOOD SPOILAGE SENSOR," published on Aug. 2, 2005; U.S. Pat. No. 6,593,142, having the title "POLYMERIC FOOD SPOILAGE SENSOR," published on Jul. 15, 2003; U.S. Pat. No. 5,454,918, having the title "COMPUTERIZED CHEMICAL INJECTION SYSTEM FOR HYDROGEN SULFIDE CONTROL IN A WASTE WATER STREAM," published on Oct. 3, 1995; and U.S. Pat. No. 4,948,727, having the title "CHEMICAL SENSOR," published on Aug. 14, 1990.

The patents, patent applications, and patent publication listed above in the preceding four paragraphs are herein incorporated by reference as if set forth in their entirety. The purpose of incorporating U.S. patents, non-U.S. patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2006 053 673.8, filed on Nov. 13, 2006, having inventor Gyula VARHANIOVSZKI, and DE-OS 10 2006 053 673.8 and 10 2006 053 673.8, and International Application No. PCT/EP2007/009634, filed on Nov. 7, 2007, having WIPO Publication No. WO2008/058659 and inventor Gyula VARHANIOVSZKI, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the Foreign equivalent patent application PCT/EP2007/009634 and German Patent Application 10 2006 053 673.8 is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2007/009634 and DE 10 2006 053 673.8 from which this patent application claims priority which do not have to do with the correction of the translation in this patent application are not to be included in this patent application in the incorporation by reference.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

1 Measuring distance and/or inspection distance, or section
2 Bottle
2.1 Bottle mouth
3 Conveyer system
4 Station for the introduction of the inspection liquid and/or control liquid
5 Nozzle tube
6 Drive arrangement
7 Stock of inspection liquid and/or control liquid
8 Measuring station
9, 9a, 9b Measuring pipe or probe pipe
10, 10a, 10b Measuring head
11 Source for measuring gas
11.1 Control valve arrangement
12 Conduit arrangement, connecting canal or channel
13 Analysis unit
14, 14a Drive arrangement
15 Control equipment
16 Sensor
17 Measuring-head housing
18, 18a Sealing element arrangement, centering element
19, 19a Opening, or recess, or canal or channel in the sealing element 18 or 18a
19.1, 19a.1 Ring canal or channel, or annular canal or channel
20, 20a Measuring-head carrier
21 Fastener element
22, 23 Pipe piece
24 Ring canal or channel, or annular canal or channel 25 Board
26 Crank wheel
27 Crank pins
28 Drive motor
29, 30 Parallelogram lever
31 Belt element
32 Double parallelogram guide arrangement
33, 34 Toothed wheel
35 Toothed belt
36, 37 Crank pins
A Transport direction of the conveyer system 3

What is claimed is:

1. A method of determining presence or absence of contamination in bottles or similar containers, said method comprising the steps of:
    introducing a first fluid medium into a container, and then introducing a second, different, fluid medium into said container, and thus forming a third fluid medium in said container;
    removing, from within said container by suction, a portion of said third fluid medium; and
    sensing said portion of said third fluid medium in a sensor apparatus to determine presence or absence of contamination in said portion of said third fluid medium.

2. The method according to claim 1, wherein said method further comprises:
    determining, in a run of containers, contaminated containers and non-contaminated containers; and
    separating said contaminated containers from said non-contaminated containers.

3. The method according to claim 2, wherein:
    said first fluid medium comprises an inspection liquid and/or control liquid, and said second fluid medium comprises a gas; and
    said step of introducing said second fluid medium comprises introducing at least one pulse of gas into said first fluid medium and at least partially nebulizing said first fluid medium in said container.

4. The method according to claim 3, wherein said step of introducing said second fluid medium comprises inserting a pipe through a mouth portion of said container into the interior of said container, and then conducting said second fluid medium through said pipe.

5. The method according to claim 4, wherein said method further comprises sealing said mouth portion of said container with a measuring head while performing said steps of introducing said second fluid medium into said container and removing said portion of said third fluid medium.

6. The method according to claim 5, wherein:
    upon at least one contaminant being present in said container, reacting said first fluid medium with said at least one contaminant and producing gaseous reaction products in said container, and then mixing said gaseous reaction products, at least in part, by said at least one pulse of gas;
    said steps of introducing said second fluid medium into said container, and removing said portion of said third fluid medium, are performed at the same time, or substantially at the same time; and
    said step of removing said portion of said third fluid comprises creating suction by underpressure.

7. The method according to claim 6, wherein:
    said at least one pulse of gas has a predetermined volume and at least one of: a predetermined duration of about thirty milliseconds, a predetermined pressure, and a predetermined temperature;
    said step of sensing said portion of said third fluid medium is performed at least twice;
    said method further comprises removing a portion of said third fluid medium from a plurality of containers and then storing the removed portions in a storage conduit, which stored portions are then analyzed; and
    said removed portions are stored sequentially.

8. The method according to claim 7, wherein:
    the portion of said third fluid medium is removed by suction through one of: said pipe and a canal formed about said pipe by said measuring head;
    said second fluid medium is sterile air;
    said container is moved on a conveyor, and said measuring head is moved, at least during delivery of said second fluid medium and removal of said portion of said third fluid medium, together with said container;
    said measuring head is moved into and out of sealing engagement by a drive arrangement configured to move said measuring head in a motion comprising both a vertical component and a horizontal component; and
    the movement of said measuring head away from said container to a second, subsequent container is determined computationally as a function of the position of said second container, and the present throughput, or production rate of the equipment with respect to accelerations, and/or delays, and/or maximum speed, and/or the respective course of these parameters, during the movement phase, at least at every change of the throughput, or production rate of the equipment.

9. The method according to claim 2, wherein:
    said first fluid medium comprises an inspection liquid and/or control liquid, and said second fluid medium comprises a gas; and
    said step of introducing said second fluid medium comprises inserting at least one pipe through a mouth portion of said container into the interior of said container, and then conducting said second fluid medium through said at least one pipe.

10. The method according to claim 9, wherein said step of introducing said second fluid medium comprises introducing at least one pulse of gas into said first fluid medium and at least partially nebulizing said first fluid medium in said container.

11. The method according to claim 2, wherein:
    said first fluid medium comprises an inspection liquid and/or control liquid, and said second fluid medium comprises a gas; and
    sealing a mouth portion of said container while performing said steps of introducing said second fluid medium into said container, and removing said portion of said third fluid medium.

12. The method according to claim 11, wherein said step of introducing said second fluid medium comprises inserting at least one pipe through a mouth portion of said container into the interior of said container, and then conducting said second fluid medium through said at least one pipe.

13. The method according to claim 1, wherein:
    upon determining the presence of at least one contaminant in said portion of said third fluid medium, determining a level of said at least one contaminant and comparing said determined level with an acceptable contaminant level stored in a memory of a control device; and
    one of (A) and (B):
    (A) removing said container from a stream of containers upon said determined level being greater than the stored, acceptable contaminant level; and (B) moving said container to a filling machine upon said determined level being equal to or less than the stored, acceptable contaminant level; and
filling said container.

14. An inspection arrangement for determining presence or absence of contamination in bottles or similar containers, said inspection arrangement comprising:
  a dispensing arrangement, a transport arrangement, and a sensor apparatus;
  said dispensing arrangement being configured to introduce a first fluid medium into a container;
  said transport arrangement being configured to introduce a second, different, fluid medium into the container containing said first fluid medium, and thus form a third fluid medium in the container, and then remove, from within the container by suction, a portion of said third fluid medium, and then transport said portion of said third fluid medium to said sensor apparatus; and
  said sensor apparatus being configured to sense said portion of said third fluid medium to determine presence or absence of contamination in said portion of said third fluid medium.

15. The inspection arrangement according to claim 14, wherein said transport arrangement comprises a measuring head, and said measuring head comprises:
  a first opening configured to deliver the second fluid medium into a container, which second fluid medium comprises a pulse of pressurized gas, to at least partially nebulize said first fluid medium in the container; and
  a second opening configured to transport said portion of said third fluid medium out of the container to said sensor apparatus.

16. The inspection arrangement according to claim 15, wherein said measuring head comprises a pipe configured to be inserted through a mouth portion of a container into the interior of then container, and configured to form said first opening to conduct said second fluid medium therethrough.

17. The inspection arrangement according to claim 16, wherein said measuring head is configured to be brought into sealing engagement with a mouth portion of a container to seal the container while said second fluid medium is introduced into the container and said portion of said third fluid medium is removed from the container.

18. The inspection arrangement according to claim 17, wherein said inspection arrangement comprises a source of pressurized gas configured to control the volume of gas delivered into each container such that each pulse has at least one of: a predetermined duration, a predetermined duration, and a predetermined temperature.

19. The inspection arrangement according to claim 18, wherein:
  said source of pressurized gas is configured to produce a pulse having a duration of about thirty milliseconds;
  said transport arrangement is configured to create suction by an underpressure;
  said transport arrangement comprises a storage comprising at least one connecting canal disposed between and to connect said measuring head and said sensor apparatus;
  said storage is configured to store a portion of said third fluid medium from a plurality of containers for subsequent analysis by said sensor apparatus;
  said measuring head forms a canal formed about said pipe, and said second opening in said measuring head is formed by one of: said pipe and said canal;
  said inspection arrangement comprises a conveyor configured to move containers, and said measuring head is configured to be moved, at least during delivery of said second fluid medium and removal of a portion of said third fluid medium, together with a container on said conveyor;
  said inspection arrangement comprises a drive arrangement configured to move said measuring head into and out of sealing engagement with a container in a motion comprising both a vertical component and a horizontal component.

* * * * *